(12) United States Patent
Robotti (10) Patent No.: US 8,076,152 B2
(45) Date of Patent: Dec. 13, 2011

(54) MICROFLUIDIC DEVICES COMPRISING FLUID FLOW PATHS HAVING MONOLITHIC CHROMATOGRAPHIC MATERIAL

(75) Inventor: Karla M. Robotti, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 12/902,008

(22) Filed: Oct. 11, 2010

(65) Prior Publication Data

US 2011/0028669 A1    Feb. 3, 2011

Related U.S. Application Data

(62) Division of application No. 11/820,856, filed on Jun. 20, 2007.

(51) Int. Cl.
C08F 20/06 (2006.01)
C08F 112/08 (2006.01)
(52) U.S. Cl. ............... 436/161; 156/292; 156/60; 156/1
(58) Field of Classification Search .................. 436/161; 422/61, 70, 50
See application file for complete search history.

(56) References Cited

U.S. PATENT DOCUMENTS

| 3,361,589 | A | 1/1968 | Lindsey |
| 5,133,840 | A | 7/1992 | Buchwalter et al. |
| 5,334,310 | A * | 8/1994 | Frechet et al. ............. 210/198.2 |
| 5,882,571 | A | 3/1999 | Kaltenbach et al. |
| 6,488,872 | B1 | 12/2002 | Beebe et al. |
| 6,783,992 | B2 | 8/2004 | Robotti et al. |
| 7,128,876 | B2 | 10/2006 | Yin et al. |
| 7,169,298 | B2 | 1/2007 | Huber et al. |
| 2002/0054835 | A1 | 5/2002 | Robotti et al. |
| 2003/0017305 | A1 | 1/2003 | Roitman et al. |
| 2003/0148291 | A1 | 8/2003 | Robotti |
| 2003/0230490 | A1 | 12/2003 | Swedberg et al. |
| 2004/0118189 | A1 | 6/2004 | Karp et al. |
| 2005/0274456 | A1 | 12/2005 | Roitman et al. |
| 2005/0274662 | A1 | 12/2005 | Xie |
| 2006/0188401 | A1 | 8/2006 | Robotti et al. |
| 2006/0219637 | A1 | 10/2006 | Killeen et al. |

OTHER PUBLICATIONS

Trojer et al. Monolithic poly(p-methylstyrene-co-1,2-bis(p-vinylphenyl)ethane) capillary columns as novel styrene stationary phases for biopolymer separation. Journal of Chromatography A. 2006, vol. 1117, No. 1, pp. 56-66.

* cited by examiner

*Primary Examiner* — Christine T Mui

(57) ABSTRACT

Aspects of the invention include a microfluidic device having a fluid flow path and a monolithic chromatographic material covalently bound to at least a portion of a polymeric surface of the fluid flow path. Aspects of the invention further include methods of making and using such devices.

17 Claims, 7 Drawing Sheets

*MS/BVPE polystyrene monolith
24 hr polymerization time*

Figure 6B

Standard CE peptide mix (9), 3.5 µl/min, 86 bar

Figure 6A

5 proteins, 3.5 µl/min, 97 bar

FIGURES 7A to 7D

MS/BVPE polystyrene monolith

MICROFLUIDIC DEVICES COMPRISING FLUID FLOW PATHS HAVING MONOLITHIC CHROMATOGRAPHIC MATERIAL

INTRODUCTION

Microfluidic technology utilizes microfeatures, such as microfluidic channels and wells, that are present in a solid structure, such as glass or polymer chips, as miniature "labs." Pressure or electrokinetic forces are employed to move picoliter volumes in a finely controlled manner through the features, e.g., channels and wells. Microfluidic technology enables sample handling, mixing, dilution, electrophoresis and chromatographic separation, staining and detection on single integrated systems, among other applications. Advantages of such technology may include ease-of-use, speed of analysis, low sample and reagent consumption and high reproducibility due to standardization and automation. As such, microfluidic technology is of great interest.

One application in which microfluidic technology finds use is chromatography. Chromatography is a method for separating a sample into individual components or analytes. In High Pressure Liquid Chromatography (HPLC), a liquid sample comprising analytes is introduced into a column under pressure. The column comprises a stationary phase with which may be provided in a variety of forms, e.g., such as an insoluble resin, beads, gel or a monolithic material. When a protein is applied to an HPLC column in a mobile phase, it equilibrates between the stationary phase and the mobile phase as it passes through the column. The speed with which a sample analyte in a mobile phase travels through the column depends on the non-covalent interactions of the analyte with the stationary phase. For example, those sample analytes that have stronger interactions with the stationary phase than with the mobile phase will elute less quickly than those analytes that have less strong interactions. Thus, in reverse phase liquid chromatography, where the stationary phase comprises a hydrophobic surface and the mobile phase is typically a mixture of water and an organic solvent, the least hydrophobic component moves through the chromatography bed first, followed by components with increasing hydrophobicity.

Examples of microfluidic devices that find use in chromatographic applications, among other applications, are provided in U.S. Pat. No. 7,128,876.

SUMMARY

Aspects of the invention include a microfluidic device having a polymeric structure with a microfluidic channel; and a monolithic chromatographic material covalently bound to at least a portion of a polymeric surface of the microfluidic channel. Aspects of the invention further include methods of making and using such devices, as well as systems and kits that include such devices.

DETAILED DESCRIPTION

Aspects of the invention include a microfluidic device having a polymeric structure with a microfluidic channel; and a monolithic chromatographic material covalently bound to at least a portion of a polymeric surface of the microfluidic channel. Aspects of the invention further include methods of making and using such devices, as well as systems and kits that include the device.

Before the present invention is described in greater detail, it is to be understood that this invention is not limited to particular embodiments described herein. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope of the present invention. Any recited method can be carried out in the order of events recited or in any other order which is logically possible.

Aspects of the invention include microfluidic devices that include a fluid flow path and a monolithic chromatographic material covalently bound to at least a portion of the surface of the fluid flow path.

The term "microfluidic device" refers to a device having features of micrometer or submicrometer dimensions, and which can be used in any number of chemical processes involving very small amounts of fluid. Such processes include, but are not limited to, electrophoresis (e.g., capillary electrophoresis or CE), chromatography (e.g., μLC), screening and diagnostics (using, e.g., hybridization or other binding means), and chemical and biochemical synthesis (e.g., DNA amplification as may be conducted using the polymerase chain reaction, or "PCR") and analysis (e.g., through enzymatic digestion).

The features of the microfluidic devices may be adapted to a particular use. For example, microfluidic devices that are used in separation processes, e.g., CE, contain fluid flow paths (e.g., channels which may be referred to as "conduits" herein when enclosed, for example when the cover plate is in place on the channel-containing substrate surface) on the order of 1 μm to 200 μm in cross-sectional dimension, such as from 10 μm to 75 μm in cross-sectional dimension, and ranging in length from 0.1 to 50 cm, such as from 1 cm to 25 cm. Microfluidic devices that are used in chemical and biochemical synthesis, e.g., DNA amplification, may include reaction zones having a volume of ranging from 1 nl to about 100 μl, such as from 10 nl to 20 μl.

Microfluidic devices of the invention contain at least one fluid flow path. The term "fluid flow path" refers to any structure configured to provide for fluid flow. The fluid flow path may be a channel, which is a passage through a substrate. The geometry of a channel may vary widely and includes tubular passages with circular, rectangular, square, D-shaped, trapezoidal or other polygonal cross-sections. A channel may comprise varying channel geometries (e.g., rectangular at one section and trapezoidal at another section). However, in one aspect, the cross-sectional area of a channel used for separation is substantially constant, e.g., in order to further reduce dead volume.

The fluid flow paths of the invention may be straight or non-straight, and may form curved or angular paths through the substrate. In addition, they may cross or intersect with other channels, and in various embodiments they can be substantially parallel to one another.

The fluid flow path of the microfluidic device is one that has a polymeric surface. Accordingly, at least the surface of the fluid flow path is made up of a polymeric material. In certain embodiments, the microfluidic device itself is made up of a polymeric material, such that the fluid flow path is present in a polymeric structure of the device and therefore has a polymeric surface. In other embodiments, the microfluidic device may be a composite structure, where the fluid flow path has a surface component made up of a polymeric material and other components, e.g., underlying layers, made up of non-polymeric materials.

In one embodiment, the microfluidic device comprises a first substrate having first and second opposing surfaces. The substrate comprises a channel formed in the first surface. In one aspect, the separation channel further comprises a monolithic chromatographic material for separating analytes according to a characteristic of the analyte (e.g., such as hydrophobicity), as described in greater detail below. A cover plate is arranged over the first surface and, in combination with the channels on the substrate, defines fluid flow paths through which fluids may flow. Alternatively, or additionally, the cover plate may comprise a channel, which is aligned with the first channel on the first surface, such that a given conduit is formed from two opposing channels.

Covers may be bonded to substrates using methods such as anodic bonding, sodium silicate bonding, fusion bonding or by glass bonding. To ensure that a conduit is fluid-tight, pressure-sealing techniques may be employed, e.g., by using external means (such as clips, tension springs or an associated clamp), by using internal means (such as male and female couplings) or by using of chemical means (e.g., adhesive or welding) to urge the pieces together. However, as with all embodiments described herein the pressure sealing techniques may allow the contacting surfaces to remain in fluid-tight contact under an internal device fluid pressure of up to 100 megapascals or greater, such as 0.5 to 40 megapascals.

Figure 1:
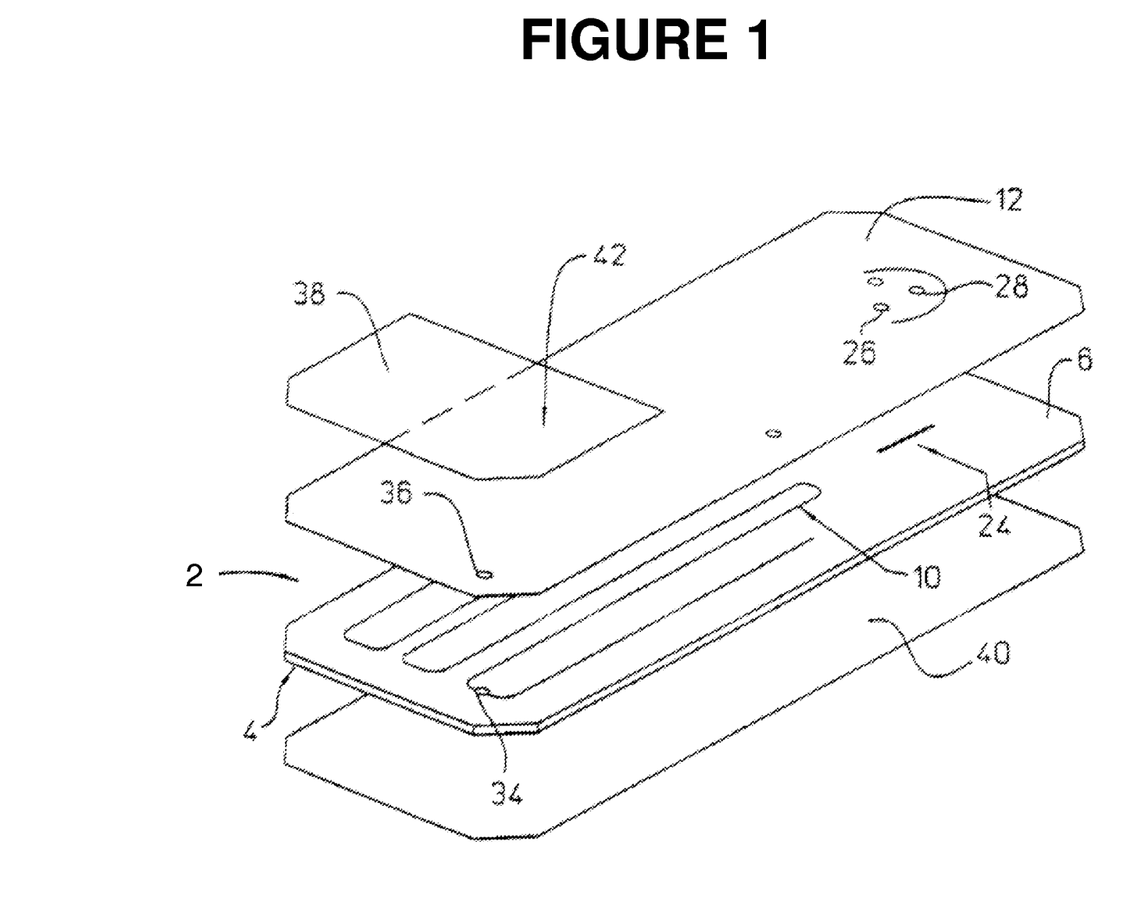
FIGS. 1 to 3 provide various views of a microfluidic device according to an embodiment of the invention.
Figure 2:
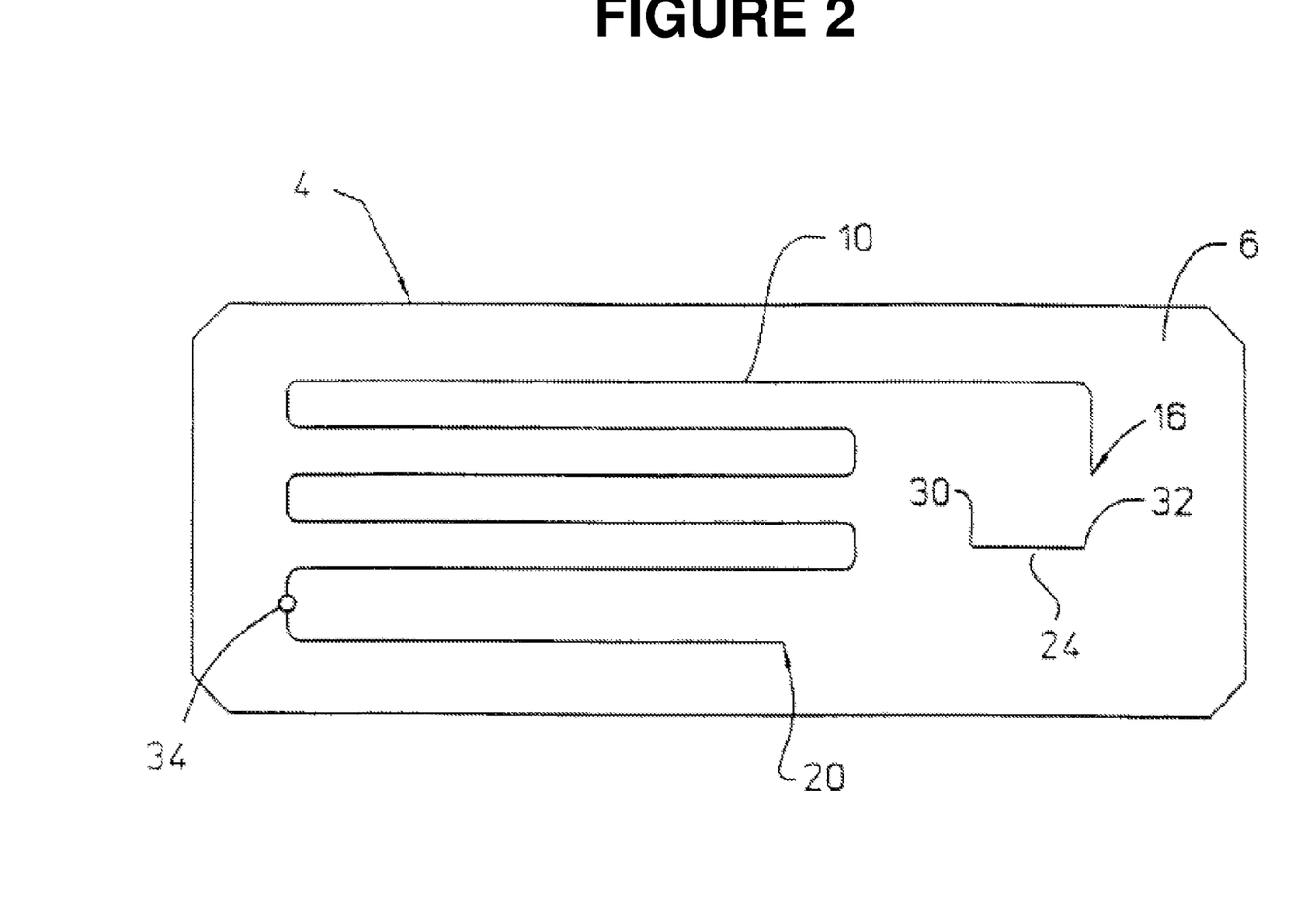
Figure 3:
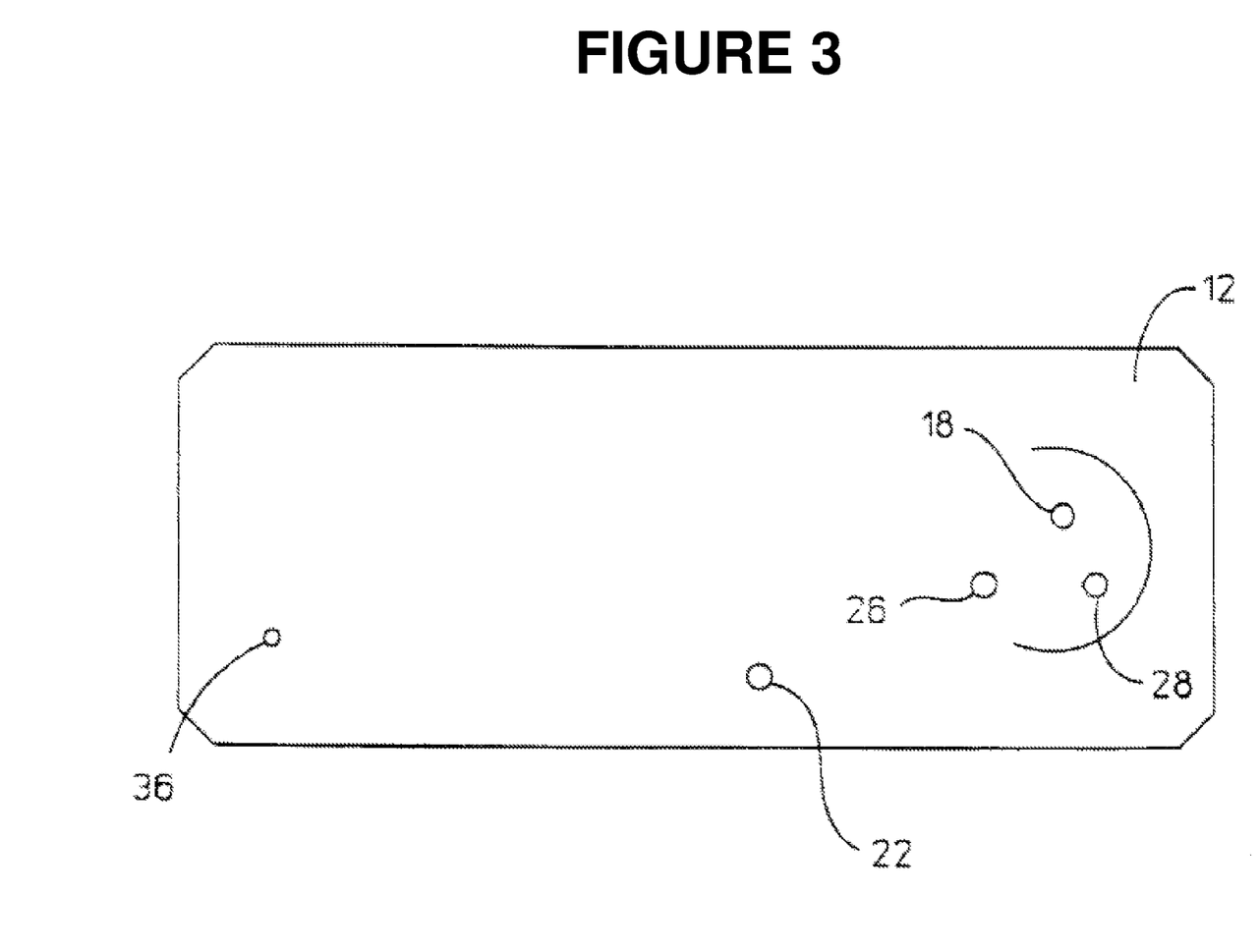

A microfluidic device according to an embodiment of the invention is shown in FIGS. 1, 2 and 3, where microfluidic device is generally indicated at 2. The device 2 is formed in a selected substrate 4 using laser ablation techniques. The substrate 4 comprises first and second substantially planar opposing surfaces indicated at 6 and 8 respectively, and is selected from a material other than silicon which is UV absorbing and, accordingly, laser-ablatable. In the embodiment shown in FIG. 1, the device 2 comprises a column structure ablated on a chip, which, in the practice of the invention may be a machinable form of polyimide, as reviewed in greater detail below. The substrate 4 has a fluid flow path 10 laser-ablated in a first planar surface 6. It will be readily appreciated that, although the fluid flow path 10 has been represented in a generally extended form, flow paths formed under the invention can be ablated in a large variety of configurations, such as in straight as well as non-straight, e.g., serpentine, spiral, or any tortuous path, formats, as desired. Further, as described above, the flow path 10 can be formed in a wide variety of channel geometries including semi-circular, rectangular, rhomboid, and the like, and the channels can be formed in a wide range of aspect ratios. A cover plate 12 is arranged over the first planar surface 6 and, in combination with the laser-ablated flow path 10, defines the enclosed fluid flow path. The cover plate 12 can be formed from any suitable substrate such as polyimide, where the selection of the substrate is limited only by avoidance of undesirable separation surfaces such as silicon or silicon dioxide materials. In various embodiments, the cover plate 12 can be fixably aligned over the first planar surface 6 to form a liquid-tight separation compartment by using pressure sealing techniques, by using external means to urge the pieces together (such as clips, tension springs or associated clamping apparatus) or by using adhesives well known in the art of bonding polymers, ceramics and the like. In the embodiments shown in FIG. 1, the cover plate 12 further includes apertures which have been ablated therein. A first aperture communicates with the enclosed flow path—which has been formed by the combination of flow path 10 and cover plate 12—at a first end 16 (see FIG. 2) thereof to form an inlet port 18 enabling the passage of fluid from an external source into the separation compartment. A second aperture communicates with the flow path at a second end 20 thereof to form an outlet port enabling passage of fluid from the separation compartment to an external receptacle. Accordingly, a miniaturized column device is formed having a flow path extending from the first end 16 of the separation compartment and passing to the second end 20 thereof, whereby liquid phase analysis of samples can be carried out using techniques well known in the art.

Referring still to FIGS. 1 to 3, a particular embodiment of the invention is shown including sample introduction means laser-ablated into both the substrate 4 and cover plate 12. An internally ablated by-pass channel 24 is formed in substrate 4, such that the channel 24 is disposed near the first end 16 of the separation compartment. Two additional apertures 26 and 28 are formed in cover plate 12 and are arranged to cooperate with first and second ends (indicated at 30 and 32 respectively) of the by-pass channel 24. In this manner, a sample being held in an external reservoir can be introduced into by-pass channel 24 to form a sample plug of a known volume (defined by the dimensions of the channel 24). The sample plug thus formed can then be introduced into the first end 16 of the enclosed fluid flow path via inlet port 18 by communicating external mechanical valving with the inlet port and laser-ablated apertures 26 and 28 and flushing solution through the by-pass channel 24 into the separation compartment.

In certain embodiments, the substrate and the cover plate may be formed in a single, solid flexible piece. Devices having a single-piece substrate and cover plate configuration have been described, e.g., in U.S. Pat. Nos. 5,658,413 and 5,882,571.

Suitable materials for forming the substrate and cover plate are selected with regard to physical and chemical characteristics that are desirable for proper functioning of the microfluidic device. In one embodiment, the substrate is fabricated from a material that enables formation of high definition (or high "resolution") features, i.e., fluid flow paths, chambers and the like, that are of micron or submicron dimensions. That is, the material is capable of microfabrication using, e.g., dry etching, wet etching, laser etching, laser ablation, molding, embossing, or the like, so as to have desired miniaturized surface features. The substrate may be capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. In certain embodiments, all device materials used are chemically inert and physically stable with respect to any substance with which they come into contact when used to introduce a fluid sample (e.g., with respect to pH, electric fields, etc.). Suitable materials for forming the present devices include, but are not limited to, polymeric materials, ceramics, glass and metals, composites and laminates thereof. Where the device is not entirely fabricated from a polymeric material, at least a portion of the surface of a fluid flow path in the device will comprise a polymeric material.

Polymeric materials of interest include organic polymers that are homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. In certain embodiments, at least one of the substrate or cover plate may include a biofouling-resistant polymer when the device is employed to transport biological fluids. Polyimide is of interest and has proven to be a highly desirable substrate material in a number of contexts. Polyimides are commercially available, e.g., under the trade name Kapton®, (DuPont, Wilmington, Del.) and Upilex® (Ube Industries, Ltd., Japan). Polyetheretherketones (PEEK) also exhibit desirable biofouling resistant properties.

As indicated above, the devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other composite substrates include polymer laminates, polymer-metal laminates, e.g., polymer coated with copper, a ceramic-in-metal or a polymer-in-metal composite. One composite material is a polyimide laminate formed from a first layer of polyimide such as Kapton®, that has been co-extruded with a second, thin layer of a thermal adhesive form of polyimide known as KJ®, also available from DuPont (Wilmington, Del.).

In certain aspects, a substrate and/or cover of the device comprises an at least partially transparent material.

The microfluidic devices can be fabricated using any convenient method, including, but not limited to, micromolding and casting techniques, embossing methods, surface micromachining and bulk-micromachining. The latter technique involves formation of microstructures by etching directly into a bulk material, such as by using wet chemical etching or reactive ion etching ("RIE"). Surface micro-machining involves fabrication from films deposited on the surface of a substrate. An example of a surface micro-machining process is known as "LIGA." See, for example, Becker et al. (1986), "Fabrication of Microstructures with High Aspect Ratios and Great Structural Heights by Synchrotron Radiation Lithography Galvanoforming, and Plastic Moulding (LIGA Process)," Microelectronic Engineering 4(1):35-36; Ehrfeld et al. (1988), "1988 LIGA Process: Sensor Construction Techniques via X-Ray Lithography," Tech. Digest from IEEE Solid-State Sensor and Actuator Workshop, Hilton Head, S. C.; Guckel et al. (1991) J. Micromech. Microeng. 1: 135-138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—e.g., diameters—on the order of microns.

Another technique for preparing the present devices is laser ablation. In laser ablation, short pulses of intense ultraviolet light are absorbed in a thin surface layer of material. Pulse energies may be greater than about 100 millijoules per square centimeter and pulse durations may be shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation may involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) Laser Focus Electro Optics, at pp. 54-70, and in U.S. Pat. Nos. 5,291,226 and 5,305,015 to Schantz et al.

In one embodiment, the fabrication technique that is used provides for features of sufficiently high definition, i.e., microscale components, channels, chambers, etc., such that precise "microalignment" of these features is possible, i.e., the features are capable of precise and accurate alignment, including, for example, the alignment of complementary channels with each other, the alignment of projections and mating depressions, the alignment of grooves and mating ridges, and the like. In one aspect, a feature for alignment on a first substrate may be mated to a receiving feature on one or more covers and/or additional substrates. In this way, a cover and/or substrate may be aligned. As defined herein, a receiving feature is any feature that can be associated with an aligning feature. For example, a receiving feature that can be associated with a projection or ridge may comprise a depression or groove while a receiving feature, which can be associated with a depression or groove, may comprise a projection or ridge. A receiving feature may be any feature of suitable geometry that may maintain alignment of a cover or substrate during a procedure on a substrate of the device such as a separation procedure.

The geometry and dimensions of fluid flow paths can be varied to suit a particular application. For example, for an LC conduit, a shorter channel will decrease the distance over which sample bands must be transported, but generally the channel should be long enough to provide adequate separation of sample bands given a particular separation methodology being used.

As summarized above, at least a portion of the polymeric surface of a fluid flow path of the microfluidic devices of the invention has a monolithic chromatographic material covalently bonded thereto. By monolithic chromatographic material is meant a material that is configured as a singular mass. As such, the material is not made up of two or more distinct masses, such as is found in chromatographic materials that are made up of a plurality of discrete beads. The monolithic material is covalently bound to at least a portion of a polymeric surface of the fluid flow path. In certain embodiments, the material fills a length of the fluid flow path. By "fills" is meant that it completely occupies the fluid flow path in the length where it is positioned, such that there is no space in the length where the material is not present. As the monolithic chromatographic material is covalently bound to the surface of the fluid flow path, it is immobilized relative to the flow path. Embodiments of the invention are characterized in that that no retaining mechanisms, such as frits, are employed to maintain the chromatographic material in the desired position in the fluid flow path. The material remains immobilized relative to the fluid flow path surface even under high pressure conditions, e.g., under applied pressures of 200 bar or more, such as 400 bar or more and include 800 bar or more.

The chromatographic material may be present in the entire fluid flow path, or a portion of the length thereof, where in certain embodiments the chromatographic material occupies 25% or more of the length of the fluid flow path, such as 50% or more of the length of the fluid flow path, including 75% or more, 85% or more, 90% or more, etc., of the length of the fluid flow path, including the entire length of the fluid flow path. The length of the fluid flow path is defined from the beginning of the path to the end of the path, where the beginning of the path has a fluid inlet and the end of the path has a fluid outlet (where the outlet may open into another distinct feature of the device, e.g., a chamber (such as a waste chamber) or provide an exit out of the device). In those embodiments where only a portion of the fluid flow path is occupied by the chromatographic material, such flow paths may be produced by functionalizing the desired portion of the flow path (e.g., as described below in greater detail) and then producing the chromatographic material on the functionalized portion.

The monolithic chromatographic material has a porosity that is suitable for use in chromatographic applications. In certain embodiments, the porosity ranges from 0.5 nm to 4000 nm, such as 1 nm to 2000 nm and including 2 nm to 1500 nm, as determined using the protocol of mercury intrusion porosimetry or scanning electron micrographs. Alternatively, a method of gel permeation chromatography (Anal. Chem., 1984, 56, 950) may employed to determine pore sizes. The monolithic chromatographic material has a permeability that makes the material suitable for chromatographic applications in a microfluidic device format, where the permeability is determined by the observed flow rate of a pure solvent to traverse the material under an applied back pressure of 10 bar to 200 bar. Flow rates range from 0.5 to 20 µl/min, such as 1 to 6 µl/min are observed in certain embodiments.

Embodiments of the chromatographic material are characterized by exhibiting substantially little, if any, swelling propensity. Swelling propensity is determined using the following formula:

$$\text{Swelling Propensity}(SP) = \frac{p(ACN) - p(H20)}{p(H20)}$$

where:

$$p = \frac{P(\text{back pressure})}{h(\text{viscosity})}$$

ACN is acetonitrile as reported in Journal of Chromatography, 350 (1985), pp 145-150. Using this formula, the swelling propensity of the material in certain embodiments is 0.9 or less, such as 0.3 or less, and including 0.09 or less, where a swelling propensity of 0 means no shrinkage or swelling.

The nature of the monolithic chromatographic material may vary depending on the intended application of the device. The monolithic chromatographic material is, in certain embodiments, fabricated from a monofunctional vinyl monomer, a di- or multifunctional vinyl monomer (which may serve as a crosslinker), an initiator and a porogen, which components (i.e., precursor reagents) are combined into a polymerization mixture and polymerized to produce the monolithic chromatographic material, as reviewed in greater detail below. The identity of the reagent precursors in the polymerization mixture dictates the nature of the chromatographic material. Suitable monomers for the above process include, but are not limited to, mono, di- and multiple functional monomers that contain vinyl functional groups.

Monovinyl monomers of interest include styrene and its derivatives containing hydroxyl, halogen, amino, sulfonic acid, carboxylic acid, nitro groups and different alkyl chains such as C4, C8, C12 and C18, or their protected format which could be used to generate those functionalities before or after polymerization. In these embodiments, the monolithic chromatographic material is a styrenic material because it is fabricated from a styrenic monomer.

Additional monomers of interest include, but are not limited to, acrylates, methacrylates, acrylamides, methacrylamides, vinylpyrolidones, vinylacetates, acrylic acids, methacrylic acids, vinyl sulfonic acids, and the derivatives or these groups which could be used to generate these compounds in situ. In these embodiments, the monolithic chromatographic material is an acrylate material.

In certain embodiments, the microfluidic device having a fluid flow path comprising a monolithic chromatographic material covalently bound to at least a portion of a surface thereof has a chip configuration. By "chip" configuration is meant that the device comprising the fluid flow path has a configuration that approximates a standard glass microscope slide. In certain of these embodiments, the length of the device ranges from 5 mm to 200 mm, such as from 20 to 90 mm, the width of the device ranges from 5 mm to 50 mm, such as from 15 to 30 mm and the height of the device ranges from 0.05 to 1 mm, such as from 0.1 to 0.3 mm.

In addition to the chromatographic material comprising fluid flow path, the microfluidic device may include additional components, such as a sample inlet port to allow a fluid sample to be introduced from a sample source into the fluid flow path, where the fluid is to be conveyed in a defined sample flow path such that the fluid sample travels, in order, through the sample inlet port, the material comprising fluid flow path and a sample outlet port. An integrated fluid introduction element may also be provided, for controllably introducing a volume, which may be predetermined, of the fluid sample from a sample source into the sample inlet port and through the fluid flow path without need for an electric field. The integrated fluid introduction element may control fluid introduction mechanically.

In addition to the above components, the device can comprise a plurality of fluid-transporting features that may be connected in a variety of geometries. For example, the device may comprise 2 or more, 4 or more, 8 or more, 16 or more, 32 or more, 48 or more, or 96 or more fluid-transporting features in addition to the material comprising fluid flow path described above. In one aspect, the number of features corresponds to the number of wells in an industry standard microtiter plate. In another aspect, the center-to-center distance between features may correspond to the center-to-center distance of wells in an industry standard microtiter plate. In certain aspects, each feature comprises a sample introduction means which communicates, either directly or indirectly with the material comprising fluid flow path.

Additional conduits can be provided for performing additional separation procedures. For example, in addition to chromatographic separation procedures, conduits can be provided for electrophoretic, diffusion-based and/or affinity-based separations. In one aspect, the device is used for multi-dimensional chromatographic separation. The device may be used to perform at least two different types of separation, selected from the group consisting of chromatographic, electrophoretic, diffusion-based, and affinity-based separation. These are merely examples, and other combinations may be envisioned and are included within the scope of the invention.

In certain embodiments, the geometry of fluid-transporting features is selected to allow for serial separation or parallel sample separation. For example, first and second conduits can be provided. In one aspect, a sample inlet port is in fluid communication with a valve (or other mechanism for controlling fluid flow) and the valve is constructed for providing selective fluid communication between the inlet-port and either one of the conduits. Valve types of interest include, but are not limited to, ball valves, solenoid valves and gate valves. In one aspect, a valve is constructed which is an integrated portion of the device. Controlling voltage differences and/or pressure differences in various portions of the device also can be used to achieve the same effect.

In certain aspects, the device comprises a fluid-transporting feature for sample processing prior to or after transport through the chromatographic material comprising fluid flow path or other conduits of the device. In certain aspects, the sample-processing fluid-transporting feature may comprise a reagent which includes but is not limited to: an enzyme, polymerase, cleaving agent, binding partner, e.g., nucleic acid binding protein, transcription factor, cofactor, receptor, ligand, helicase, topoisomerase, antibody, labeling reagent, derivatizing agent, dye, cell, ions (e.g., for altering pH of a fluid), etc. A sample-processing feature may be in communication with an inlet port for introducing the agent. The sample-processing fluid-transporting feature may also be in communication with a device for altering a condition of a fluid in the feature, for example such as a heating or cooling element, or a light source. Sample processing features may be upstream or downstream of the fluid flow path.

In certain aspects, the device comprises one or more sample-holding reservoirs or conduits, which may at least transiently hold a sample. In one aspect, a sample-holding reservoir provides a compartment within the device wherein a sample-processing event may occur, i.e., the sample-holding reservoir may also be a sample-processing reservoir. Further, in additional aspects, aliquots of a sample may be exposed to an agent (e.g., such as a cleaving agent) in the sample-holding reservoir for different intervals of time, and then otherwise subjected to the same sample fluid processing/separating conditions, e.g., in parallel fluid-transporting features of the device.

In another embodiment, the device comprises one or more focusing elements for concentrating a sample. For example, the device may comprise a pH gradient establishing element within a fluid flow path. In one aspect, at least one separation medium in at least one fluid flow path is used to establish a pH gradient in the path. For example the focusing feature may be a conduit in communication at one end with a fluid-transporting feature (e.g., a reservoir) comprising an ampholyte. Electrodes can be used to generate an electric field in the ampholyte-containing fluid-transporting feature. The acidic and basic groups of the molecules of the ampholyte will align themselves accordingly in the electric field, migrate, and in that way generate a temporary or stable pH gradient. A fluid-transporting feature downstream can be used to collect concentrated or focused biopolymer molecules that have passed through the gradient.

In certain embodiments, the microfluidic device has the structure of an HPLC-Chip as sold by Agilent Technologies (Santa Clara, Calif.), where a fluid flow path of the HPLC-Chip device is as described above.

In one embodiment, the microfluidic device is present in a fluid processing system that includes a detector. In one aspect, the detector is placed in proximity to a monolithic chromatographic material comprising fluid flow path to enable a user to monitor separation efficiency and/or sample characteristics. In certain aspects, a plurality of detectors is interfaced with the system. For example, detectors may be placed at various flow points of the system to enable a user to monitor separation efficiency, and may be in proximity to both a first and second monolithic chromatographic material comprising fluid flow path. Detectors may monitor changes in molecular weight, refractive index, ultraviolet and/or visible light absorption, light scattering or fluorescence after excitation of a sample (e.g., a solution comprising proteins) with light of a suitable wavelength.

Detectors additionally can be coupled to cameras, appropriate filter systems, and photomultiplier tubes. The detectors need not be limited to optical detectors, but can include any detector used for detection in liquid chromatography and capillary electrophoresis, including electrochemical, conductivity, and the like.

In another embodiment, the system comprises an analysis system for analyzing separated component(s) in a sample that has flowed through at least one monolithic chromatographic material comprising fluid flow path of the device. In one aspect, the analysis system comprises, or is connectable to, a processor for obtaining signals from a detector and converting these to data relating to properties of molecules being separated. The detector and/or analysis system may be directly or indirectly coupled to the device. In one embodiment, an electrospray device is interfaced with a device according to aspects of the invention and delivers separated or at least partially separated molecules (e.g., such as peptides) to a detector/analysis system such as a mass spectrometry device. Electrospray of interest include those described in Wilm and Mann, Anal. Chem. 1996; 68: 1-8; Ramsey et al., Anal. Chem. 1997; 69: 1174-1178; Xue et al., Anal Chem. 1997; 69: 426-430; and U.S. Pat. No. 6,245,227.

In one aspect, a device according to the invention comprises an integrated electrospray emitter such as described in U.S. Patent Publication 20040156753. In the case where the protein analysis system comprises a MALDI device, an automated spotter may be used to provide an interface with the MALDI device.

In other aspects, the monolithic chromatographic material comprising fluid flow path is in fluid communication with a collector, such as a sample vial, plate, or capillary or with another fluid-transporting feature for communication with another separation conduit on the same or a different substrate of the device. A collector may serve as a storage device or represent an intermediary to another device that uses and/or analyzes collected sample fractions.

Mass spectrometry technologies may involve, for example, laser desorption and ionization technologies, whose use in conjunction with devices are described in U.S. Pat. Nos. 5,705,813 and 5,716,825. In the alternative or in addition, the analysis system may comprise a source of electromagnetic radiation configured to generate electromagnetic radiation of a predetermined wavelength. Depending on the intrinsic properties of the fluid sample and/or any molecular labels used, the radiation may be ultraviolet, visible or infrared radiation.

In one aspect, the analysis system comprises or is in communication with a processor for determining the biopolymeric sequences, e.g., amino acid sequences, of biopolymer digestion products, e.g., protein digestion products or peptides, and/or for correlating mass/charge properties of products or derivatives thereof (or ionized fragments thereof) with a corresponding reference, e.g., protein, from which the product (or derivative thereof) derives. Also of interest are embodiments configured for nucleic acid analysis.

In another aspect, the system further comprises a memory in which data relating to molecules separated by devices according to the invention may be stored. The processor may be used to monitor and/or control other system functions, e.g., such as the opening or closing of valves or changes in potential in one or more fluid-transporting features.

In certain embodiments, the microfluidic device is part of an analysis system chosen from the Agilent 1200 Series nanoflow LC, the Agilent 6300 Series LC/MSD Trap XCT Ultra and the Agilent 6210 Series LC/MSD TOF systems (all available from Agilent Technologies, Santa Clara, Calif.).

The invention further provides methods for using devices and systems disclosed herein.

Methods of invention include those where a fluid, e.g., sample, is flowed through a monolithic chromatographic material comprising fluid flow path of a microfluidic device. Movement of the sample through the fluid flow path may be under applied pressure, where an applied pressure may range from 5 bar to 400 bar, such as from 10 to 180 bar. In one embodiment, a method according to the invention comprises introducing a mobile phase through a monolithic chromatographic material comprising fluid flow path of a microfluidic device at a first flow rate, then introducing a mobile phase through the fluid flow path at a second, slower flow rate. In another aspect, change in the flow rate of the mobile phase is produced by selectively diverting a portion of the mobile phase to a waste reservoir, while permitting the remainder of the mobile phase to be introduced into the fluid flow path. In still another aspect, selective diverting or splitting of the mobile phase is implemented by way of a switching structure which selectively connects fluid-transporting features on the device and/or on the switching structure at selected times. In a further aspect, the mobile phase comprises a gradient of a mobile phase component.

In one embodiment, a mobile phase gradient and sample are introduced into a monolithic chromatographic material comprising fluid flow path of a microfluidic device without previously splitting the mobile phase. After sample components are eluted (e.g., the last peak from a sample is detected by a detection system in suitable proximity to the device), mobile phase flow is increased. A portion of the mobile phase is then diverted to a waste reservoir, while the remainder continues to flow, at a lower rate to the fluid flow path. Sample components in the remainder of the mobile phase are eluted from the fluid flow path. In one embodiment, a switching structure is used to selectively control communication between different fluid-transporting features of the device.

Samples flowing through a monolithic chromatographic material comprising fluid flow path of a microfluidic device may be evaluated by an analysis system as described above. In one aspect, the fluid flow path communicates with a downstream conduit that splits in two paths, one which connects with a second conduit and one which connects with the same or a different analysis system such that an aliquot of the separated sample may be evaluated by the analysis system while an another aliquot is subjected to further separation and/or analysis by the same or a different analysis system. In certain embodiments, the second conduit comprises or is connected to a conduit that also splits into two paths, one path which permits a portion of a sample to be analyzed by an analysis system and a second path which may permit further or a different type of analysis or may permit isolation of components of the sample. Movement to and from separating channels and other fluid transporting features can be controlled using mechanisms known in the art, for example, through pressure-modifying mechanisms and/or through electroosmotic or electrokinetic flow-controlling mechanisms.

In one aspect, the choice of buffers and reagents in the upstream separation conduit will be optimized to be compatible with downstream fluid-transporting features with which it communicates. For example, a buffer or solvent may be selected which maintains the solubility of molecules in a sample while not substantially affecting processes occurring in downstream conduit(s). Conduits for providing dilution buffers and/or exchange matrices may be included at appropriate locations/flow paths in the device to dilute/exchange fluids and components in fluids as appropriate.

Methods of the invention find use in a variety of applications, which applications may be viewed as sample analysis applications. In certain embodiments, the applications are chromatographic applications. A variety of different samples may be analyzed by methods of the invention, where such samples include, but are not limited to: biological samples, environment samples, food samples, etc.

Aspects of the invention further include methods of making microfluidic devices that include a monolithic chromatographic material comprising fluid flow path, e.g., as described above. Aspects of methods of the invention include providing a microfluidic device fluid flow path wherein at least a portion of the path has a functionalized polymeric surface with a polymerization mixture of precursor reagents of a monolithic chromatographic material to be produced in the fluid flow path; and then polymerizing the polymerization mixture.

In certain embodiments, the precursors of the polymerization mixture include mono- and multifunctional monomers (e.g., di- or tri-functional monomers), a polymerization initiator and porogen(s). Suitable monomers for the above process include, but are not limited to mono, di- and multiple functional monomers, such as monomers containing vinyl functional groups, which might be generated in situ as an intermediate.

Suitable mono-functional monomers include monovinyl monomers, where such monomers include, but are not limited to, styrenic monomers such as stryrene and its derivatives, where the monomers may contain hydroxyl, halogen, amino, sulfonic acid, carboxylic acid, nitro groups and different alkyl chains such as C4, C8, C12 and C18, or their protected format which could be used to generate those functionalities before or after polymerization.

Suitable monomers for the above process also include, but are not limited to, include acrylic monomers, such as acrylates, methacrylates, acrylamides, methacrylamides, vinylpyrolidones, vinylacetates, acrylic acids, methacrylic acids, vinyl sulfonic acids, and the derivatives or these groups which could be used to generate these compounds in situ.

A given polymerization mixture may include a single type of monomer, or a mixture of a two or more different types of monomers.

In the polymerization mixture, the amount of the monofuntional monomer(s) present may vary, where in certain embodiments the amount ranges from 10 to 25%, such as 15 to 20% and including from 17 to 19% (v/v).

Also present may be a di- or multifunctional monomer(s), which precursor component serves as a cross-linking agent. Of interest are di- or multiple vinyl-containing monomers with a bridging moiety such as benzene, naphthalene, pyridine, alkyl ethylene glycol or its oligomers. Examples of these polyvinyl compounds are divinylbenzene, divinylnaphthalene, alkylene diacrylates, dimethacrylates, diacrylamides and dimethacrylamide, divinylpiridine, ethylene glycol dimethacrylates and diacrylates, polyethylene glycol dimethacrylates and acrylates, pentaerythritol di-, tri-, or tetramethacrylate and acrylate, trimethylopropane trimethacrylate and acrylate, and the mixture of these compounds.

In the polymerization mixture, the amount of the di- or multi-funtional monomer(s) present may vary, where in certain embodiments the amount ranges from 10 to 25%, such as 15 to 20% and including from 17 to 19% (v/v).

Also present may be an initiator. Initiators of interest include, but not limited to: azo compounds and peroxides. Example of initiators of interest are azobisisobutylonitrile, benzoyl peroxide, 2,2'-azobis(isobutyramide)dehydrate, 2,2'-azobis(2-amidinopropane)dihydrochloride. The amount of the initiator in the reaction mixture may range from 0.5 to 2%, such as 0.8 to 1.3% (v/v).

Porogens of interest are any material or compound that can be removed after polymerization to generate separation-effective opening structures. Porogens that may be used include, but are not limited to: organic solvents, water, oligomers, polymers, decomposable or soluble polymers. Some examples of the organic solvents are alcohols, esters, ethers, aliphatic and aromatic hydrocarbons, ketones, di-, tri- and tetraethylene glycols, butane diols, glycerols or the combination of these solvents. The choice of porogen depends on the separation-effective opening size and separation-effective opening distribution needed. In some embodiments, a single or a combination of porogenic solvents is chosen. The single or a combination of porogenic solvents is mixable with the monomers and initiators to form a homogeneous fluid mixture but the single or a combination of porogenic solvents have poor solvating power with the polymers formed. The amount of the porogen precursors in the reaction mixture may range from 50 to 80%, such as 55 to 70% (v/v).

Following preparation of the polymerization mixture, the polymerization mixture is positioned inside the fluid flow path of the microfluidic device at the desired location. The desired location (e.g., length of fluid flow path) into which the polymerization mixture is positioned is one where the surface displays an appropriate functional group, e.g., a vinyl or activated double bond functionality, which will covalently bond to the monolithic chromatographic material prepared from the polymerization mixture during polymerization. The polymerization mixture may be positioned into the desired region of the flow path using any convenient approach, e.g., by introducing the polymerization mixture into inlet port of the device and applying a suitable back pressure to move the mixture into the fluid flow path.

Following positioning of the polymerization mixture in the fluid flow path, the polymerization mixture is polymerized to produce the monolithic chromatographic material. To polymerize the polymerization mixture, the mixture is subjected to a suitable stimulus for a time sufficient to provide the desired product.

In certain embodiments, the stimulus is heat. The polymerization temperature depends on the choice of initiator. For example, when AIBN and Benzoyl Peroxide are used as initiators, a suitable temperature range is from 50 to 90° C. The heating source can be any convenient source, e.g., a jig as described in the Experimental Section, below. The reaction time can vary, and ranges in certain embodiments from 0.5 to 24 hours depending on the choice of initiator and reaction temperature and desired final monolithic application.

In certain embodiments, the stimulus employed is irradiation. Irradiation, such as IR, UV-vis or X-ray, is used as the source for polymerization when a light sensitive initiator is used. In one embodiment the reaction starts the application of energetic radiation such as X-rays, either with or without a chemical initiator. If X-rays are used, the initiator should be selected to thermally activate at temperatures well above the polymerization temperature. On the other hand, the initiator activates when under X-ray irradiation at temperatures in the given region desirable for the reaction mass to receive activation. The initiator is also selected so that activation time and temperature for dissociation is considerably less than for the monomers alone. The production of active initiator (free radical) is controlled only by the X-ray's intensity. Moreover, the initiator may be chosen to activate when under X-ray irradiation at temperatures in the given region desirable for the reaction mass to receive activation. In one embodiment, X-rays supply all or part of the energy for polymerization. The energy of the X-ray photons may be varied in accordance with the preparation of the polymers and with the difference in thickness or cross-sections. Lower energy X-rays are used for preparation of smaller diameter polymer rods and higher energy X-rays or exposure to lower energy X-ray for a longer period of time may be used for preparation of large diameter polymer rods.

The polymerization usually starts from the initiator. The formation of oligomers is followed by crosslinking forming crosslinked polymer or nuclei, and the continuous growth of the polymer or nuclei. These polymer chains and nuclei precipitate out of the liquid mixture at the size allowed by the solvating power of the porogenic solvents. These polymer chains and nuclei are suspended in the liquid mixture first and form small particles through collision and crosslinking. The small particles are swelled by the porogens and monomers, and continue to grow by both polymerization and aggregation with other nucleis or particles. The larger particles aggregate together by collision and are held in place by crosslinking.

As mentioned above, the position of the fluid flow path where the polymerization mixture is placed is one that displays a suitable functionality (e.g., a vinyl functionality) on its surface that provides for covalent attachment of the product monolithic chromatographic material to the flow path surface following polymerization.

In certain embodiments, the fluid flow path has a polyimide surface (as reviewed above) and the functionalized surface of the fluid flow path onto which the polymerization mixture is placed is a functionalized polyimide surface, such as a polyimide surface that has been functionalized to display vinyl functional groups.

Polyimide surfaces can be functionalized to display a vinyl functional group using any convenient protocol. In one embodiment, a polyimide surface is functionalized by first producing carboxylic functional groups on at least a portion of the polymide surface. Production of carboxylic acid groups may be accomplished using the following protocol. First, the polyimide surface to be functionalized is maintained under basic conditions, e.g., a pH ranging from 12 to 14 (as provided, e.g., by a solution of KOH), for a period of time ranging from 30 to 90 min. The surface is then washed, e.g., with water. The washed surface is then maintained under acidic conditions, e.g., a pH ranging from 0.7 to 1.0 (as provided, e.g., by a solution of HCl), for a period of time ranging from 5 to 8 min. The surface may then be washed again, e.g., with water, and dried, to provide a functionalized polyimide surface that displays carboxylic acid functional groups. The above steps may be carried out any convenient temperature, such as a temperature ranging from 18 to 25° C. Functionalization of a desired flow path may be accomplished using any convenient protocol. For example, where only a region of the flow path is to be functionalized, the flow path can be functionalized prior to combining a top and bottom plate together, so that the functionalization can be readily limited to the desired portion of the flow. Where the entire flow path is to be functionalized, the above protocol can be performed by sequentially flowing the various reactant fluids through the flow path.

The resultant carboxylic acid displaying functionalized surface may then be further functionalized to display the desired vinyl functional groups. One protocol of interest for this step is to maintain the surface in the presence of a suitable composition that includes vinyl moiety comprising molecule under conditions sufficient for the vinyl moiety comprising molecule to covalently bond to the surface via the carboxylic acid functional group. The composition may include any convenient vinyl moiety comprising molecule, as well as a number of additional components, e.g., coupling agents, as desired. Vinyl moiety comprising molecules of interest include, but are not limited to: allyl amine, 4-vinyl benzyl alcohol, methacryl chloride and the like. Coupling agents of interest include, but are not limited to: N-(3-Dimethylaminopropyl)-N'-ethylcarbodiimide hydrochloride (EDC); 1,3-dicarbodiimide and the like. The composition is maintained on the surface of fluid flow path for a period of time sufficient for coupling to occur, where the time may range from 20 min to 60 min. The above steps may be carried out any convenient temperature, such as a temperature ranging from 18 to 25° C.

Aspects of the invention also include kits. In some embodiments, the kits include a microfluidic device as described above. The kits may further include more additional components, such as reagents, solvents, etc., which are to be used in a given assay in which the device will be employed. The kit components may be present in separate containers, or one or more of the components may be present in the same container, where the containers may be storage containers and/or containers that are employed during the assay for which the kit is designed.

In addition to the above components, the kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another format would be a computer readable medium, e.g., diskette, CD, etc., on which the information has been recorded. Yet another format that may be present is a website address which may be used via the internet to access the information at a removed site.

The following examples are offered by way of illustration and not by way of limitation.

EXPERIMENTAL

I. Preparation of Microfluidic Device

A. Functionalization of Polyimide Microfluidic Channel Walls

A polyimide microfluidic channel of a microfluidic chip device was filled with 1N KOH solution and sealed at room temperature for 75 min. The channel was flushed with water for several minutes and then filled with a 0.2M solution of HCl and allowed to stand at room temperature for 5 min. Finally, the channel was flushed with water, then acetonitrile and dried with a stream of air.

Figure 4:
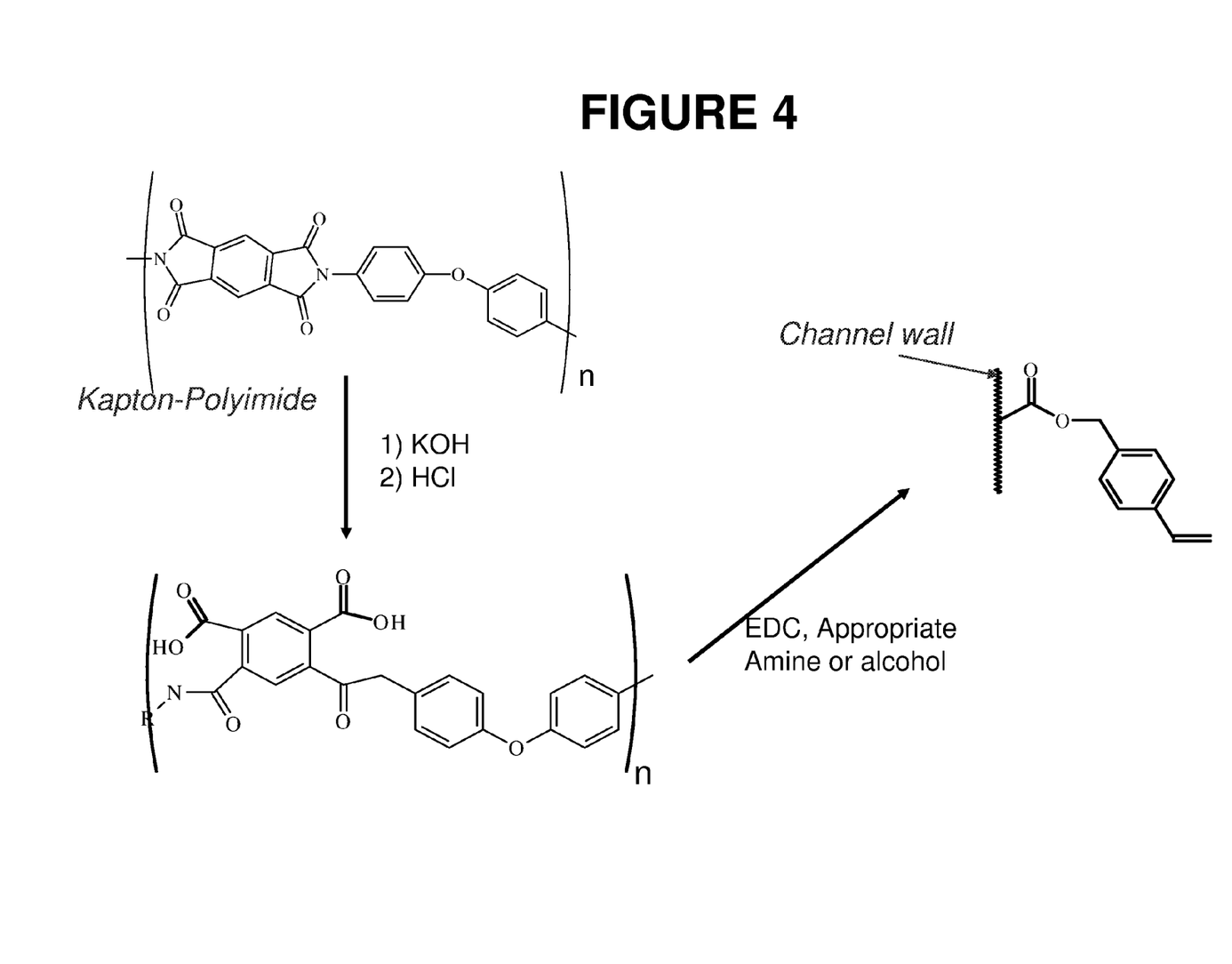
FIG. 4 provides a reaction scheme for producing a functionalized polyimide surface of a fluid flow path according to an embodiment of the invention.

A solution containing 4 mg of EDC(N-(3-Dimethylaminopropyl)-N'-ethylcarbodiimide hydrochloride, Aldrich E7750), 2 drops of water, 3 ml of acetonitrile and 4 µl of 4-vinyl benzyl alcohol (Spectrum Chemicals, V2205) was prepared. This solution was flowed into the microfluidic channel for 3 min., then the channel was sealed at room temperature for 20 min. More solution was flushed through the channel and again allowed to sit in the channel for 20 min. Finally, acetonitrile was flushed through the channel and the channel was allowed to dry with a stream of air. A schematic of the above reaction scheme is provided in FIG. 4.

The resultant microfluidic chip device included a microfluidic channel that displayed "active" vinyl functional groups on its surface.

B. Production of PS-BVPE (polystyrene-bis-(p-vinylphenyl) ethane) Monolithic Chromatographic Material within a Microfluidic Channel A microfluidic chip device produced as described in section A above was placed in a specially-designed heating jig that maintains the temperature of the chip and channels to within 1° C.

A chromatographic material precursor reagent mixture was prepared by combining 5 mg AIBN (azo-isobutryl nitrile, Aldrich 441090), 89.5 mg 1,2-bis(p-vinylphenyl)ethane, 100 µl of methyl styrene (monomer to crosslinker mass ratio 1:1), 50 µl of anhydrous toluene and 250 µl of decanol in a glass vial and the glass vial was sealed. The vial was sonicated at 50° C. for several minutes to dissolve all components. This solution was then flowed into the microfluidic channel using a warmed syringe. The channel was sealed and the chip remained at set temperature (63° C. in this case) for a period of time to polymerize the precursors into a monolithic chromatographic material. (Polymerization time ranged from 45 min. to 24 hr—depending on the end use of the monolithic column formed. The particular protocol employed was optimized for the application end-use).

Figure 5:
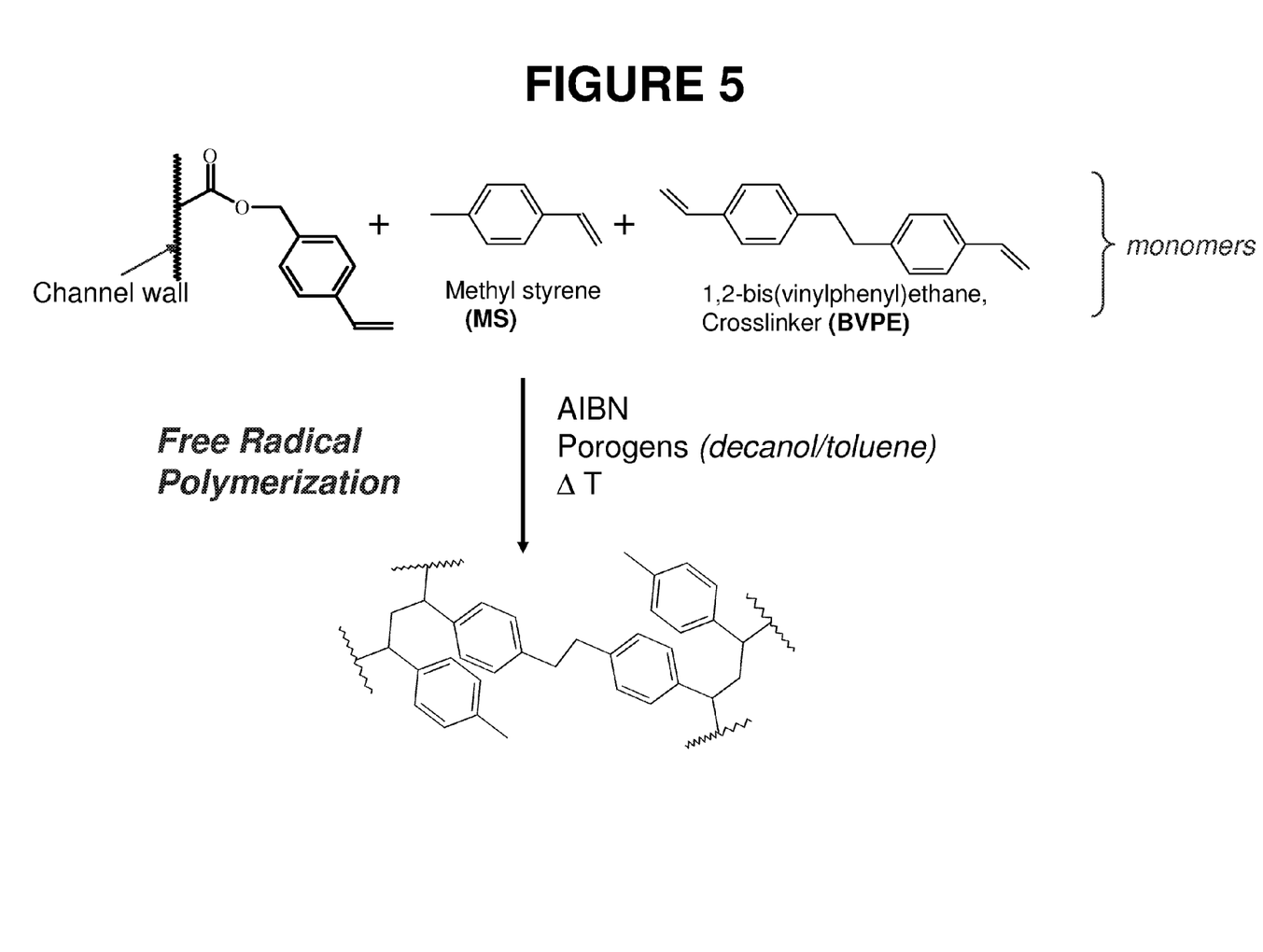
FIG. 5 provides a reaction scheme for producing a monolithic chromatographic material on a functionalized polyimide surface of a fluid flow path according to an embodiment of the invention.

After polymerization, the chip device was removed from the heat jig and cooled to room temperature. It was then purged with 100% acetonitrile for 30 min to remove any unreacted precursors, e.g., monomers, porogens, etc. A schematic of the above reaction scheme is provided in FIG. 5.

The chip was then ready to use for LC applications.

II. Characterization of Microfluidic Device

A. Liquid Chromatography of Biomolecules

A chip formed with the monolith protocol as described in Part I, B (above) was used to look at liquid chromatography (LC) of larger biomolecules, such as proteins and peptide mixtures. The monolith was polymerized for 24 hr. at 63° C. A sample of 5 proteins (ribonuclease A, cytochrome C, α-lactalbumin, β-lactoglobulin A, and ovalbumin) were combined at a concentration of 100 µg/ml each. This sample solution was injected into a microchip containing a UV cell detector. The LC was performed using a linear gradient elution of 10 to 60% solvent B to solvent A over 10 min. with a 15 min run at a flow rate of 3.5 µl/min. Solvent A was water with 0.1% TFA while solvent B was acetonitrile containing 0.1% TFA. The UV signal was monitored at 214 nm.

Another LC was performed with a commercially available sample of CE peptides (Sigma P2693) again using reverse phase conditions with a linear gradient of 10-60% solvent to solvent A over 10 min and a flow rate of 3.5 µl/min.

Figure 6A:
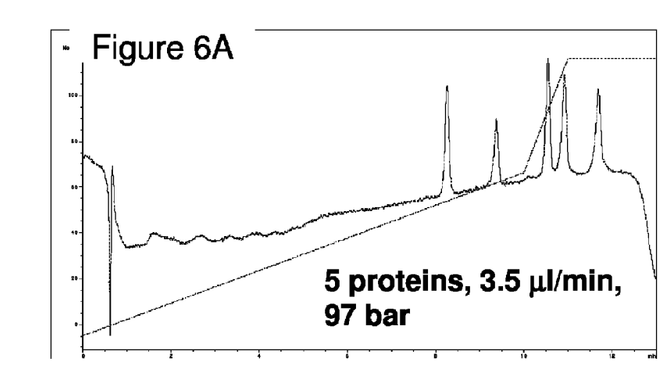
FIGS. 6A and 6B, as well as 7A to 7D, provide graphical representations of data produced from separations as described in the Experimental Section, below.
Figure 6B:
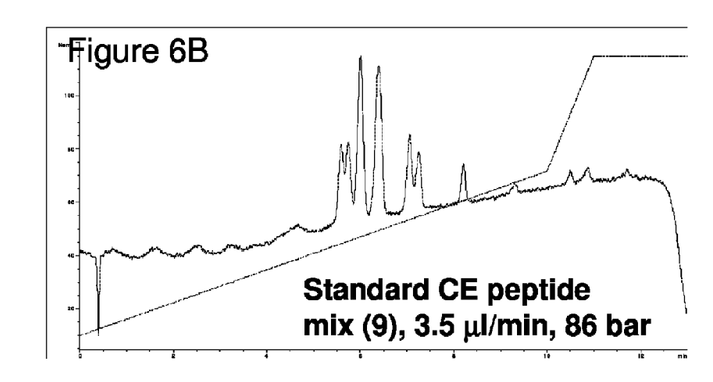
Figure 7A:
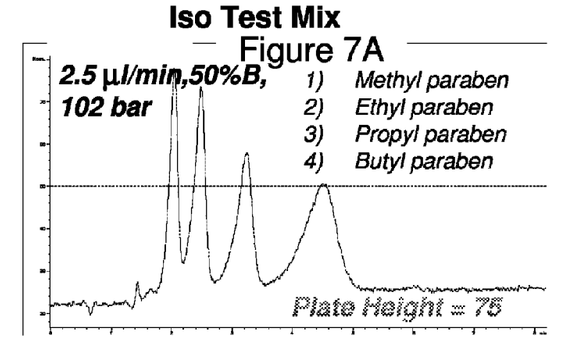
Figure 7B:
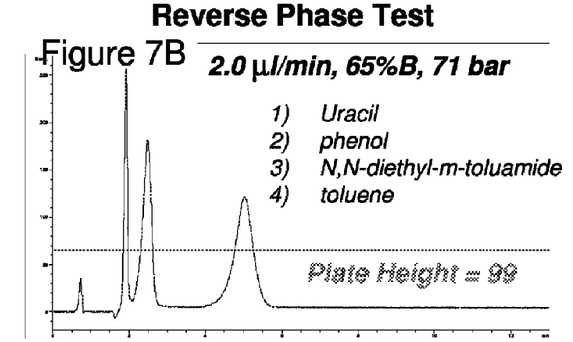
Figure 7C:
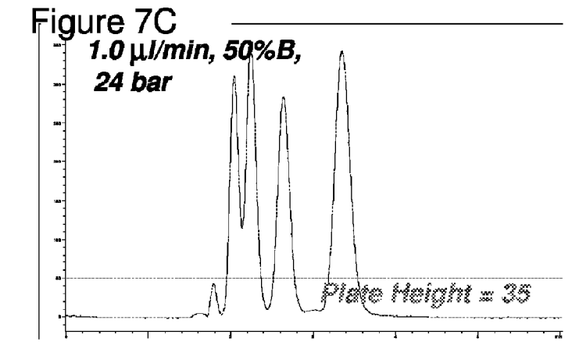
Figure 7D:
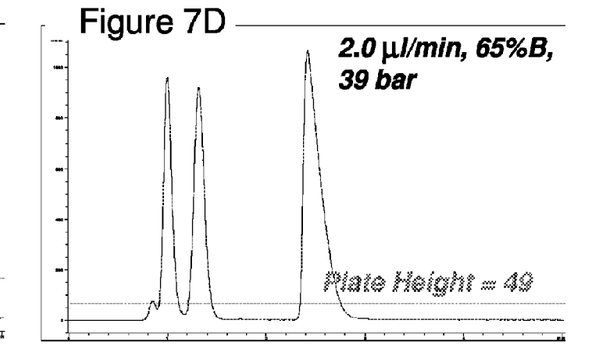

The results are shown in FIGS. 6A and 6B. As shown in FIGS. 6A and 6B, separation of the disparate proteins is achieved.

B. Liquid Chromatography of Test Mixtures

Two chips were prepared with the monolith protocol described in Part 1, B (above) but one chip was polymerized for 2 hrs, while the other was polymerized for 45 min. at 63° C. Shorter polymerization times allow separations of very small molecules with the polystyrenic monoliths. Two commercial test samples were used: a) an isocratic text mixture (Supelco #48270-U) of 4 parabens and b) a reverse phase test mix (Supelco #4-7641). The isocratic sample was run at 50% solvent B to solvent A at a 2.5 µl/min flow rate with the 2 hr chip and at 1 µl/min on the 45 min. chip. The LC of the reverse phase samples were run with 65% solvent B to solvent A at 2 µl/min flow rate on both the 2 hr chip and the 45 min. chip. The plate heights (i.e., plate number) are noted on the chromatograms.[1] UV was monitored at 254 nm.

[1] The plate height or plate number has its conventional meaning and is a number indicative of column performance, calculated from the following equations which depend on the selection of the peak width expression:

$$N=(VR/\sigma)^2=(tR/\sigma)^2$$

$$N=16(VR/wb)^2=16(tR/wb)^2$$

$$N=5.545(VR/wh)^2=5.545(tR/wh)^2$$

The value of 5.545 stands for 8 ln 2. These expressions assume a Gaussian (symmetrical) peak. In these expressions the units for the quantities inside the brackets are consistent so that their ratio is dimensionless: i.e. if the numerator is a volume, then peak width is also expressed in terms of volume. IUPAC Compendium of Chemical Terminology 2nd Edition (1997)

The results are provided in FIGS. 7A to 7D. As shown in Figure FIGS. 7A to 7D, separation of the mixtures was achieved.

Although the foregoing invention has been described in some detail by way of illustration and example for purposes of clarity of understanding, certain changes and modifications may be made thereto without departing from the scope of the appended claims.

What is claimed is:

1. A method of producing a microfluidic device comprising a fluid flow path comprising a chromatographic material, said method comprising:
   (a) filling at least a portion of said fluid flow path having a functionalized polymeric surface with a polymerization mixture of precursor reagents of a monolithic chromatographic material; and
   (b) polymerizing said polymerization mixture to produce a microfluidic device comprising a monolithic chromatographic material covalently bound to at least a portion of said polymeric surface of said fluid flow path.

2. The method according to claim 1, wherein said precursor reagents comprise monomers.

3. The method according to claim 2, wherein said monomers are styrenic monomers.

4. The method according to claim 2, wherein said monomers are acrylic monomers.

5. The method according to claim 1, wherein said precursor reagents comprise a porogen.

6. The method according to claim 1, wherein said polymerizing comprises applying heat to said polymerization mixture.

7. The method according to claim 1, wherein said functionalized polymeric surface is a functionalized polyimide surface.

8. The method according to claim 7, wherein said method further comprises preparing said functionalized polyimide surface by a method comprising:
   providing a microfluidic device comprising a fluid flow path having a polyimide surface; and
   producing carboxylic acid functional groups on at least a portion of said polymide surface to produce said functionalized polyimide surface.

9. The method according to claim 8, wherein said carboxylic acid functional groups are produced by contacting said portion with a basic fluid for a period of time sufficient to produce said carboxylic acid functional groups on said portion.

10. The method according to claim 9, wherein said basic fluid is potassium hydroxide.

11. The method according to claim 9, wherein said carboxylic acid functional groups are produced by contacting said portion with an acidic fluid after contacting said portion with said basic fluid.

12. The method according to claim 11, wherein said acidic fluid is hydrochloric acid.

13. The method according to claim 11, wherein said method further comprises producing vinyl functional groups on a least a portion of said polyimide surface.

14. The method according to claim 13, wherein said vinyl functional groups are styrenic functional groups.

15. The method according to claim 13, wherein producing said vinyl functional groups comprises contacting said carboxylic acid functional groups with a carbodiimide and a vinyl alcohol or a vinyl amine for a period of time sufficient to produce said vinyl functional groups.

16. The method according to claim 15, wherein said carbodiimide is N-(3-dimethylaminopropyl)-N'-ethylcarbodiimide.

17. The method according to claim 15, wherein said vinyl alcohol is 4-vinyl-benzyl alcohol.

* * * * *

UNITED STATES PATENT AND TRADEMARK OFFICE
CERTIFICATE OF CORRECTION

PATENT NO. : 8,076,152 B2
APPLICATION NO. : 12/902008
DATED : December 13, 2011
INVENTOR(S) : Karla M. Robotti Page 1 of 1

It is certified that error appears in the above-identified patent and that said Letters Patent is hereby corrected as shown below:

On the Title page, in field (54), in "Title", in column 1, line 2, delete "HAVING" and insert -- HAVING A --, therefor.

In column 1, line 2, delete "HAVING" and insert -- HAVING A --, therefor.

In column 18, line 36, in Claim 8, delete "polymide" and insert -- polyimide --, therefor.

In column 18, line 53, in Claim 13, delete "a least" and insert -- at least --, therefor.

Signed and Sealed this
Fourteenth Day of February, 2012

David J. Kappos
*Director of the United States Patent and Trademark Office*